(12) United States Patent
Geistlich et al.

(10) Patent No.: US 6,576,015 B2
(45) Date of Patent: Jun. 10, 2003

(54) BONE MATERIAL AND COLLAGEN COMBINATION FOR REPAIR OF INJURED JOINTS

(75) Inventors: Peter Geistlich, Stansstad (CH); Lothar Schloesser, Darmstadt (DE)

(73) Assignee: Ed. Geistlich Soehne AG fuer Chemische Industrie (CH)

( * ) Notice: Subject to any disclaimer, the term of this patent is extended or adjusted under 35 U.S.C. 154(b) by 0 days.

(21) Appl. No.: 09/906,802

(22) Filed: Jul. 18, 2001

(65) Prior Publication Data
US 2002/0013626 A1 Jan. 31, 2002

Related U.S. Application Data
(60) Provisional application No. 60/219,009, filed on Jul. 19, 2000.

(51) Int. Cl.$^7$ .................................................. A61F 2/28
(52) U.S. Cl. ...................... 623/16.11; 623/16.11; 424/426; 424/422; 424/423; 523/511
(58) Field of Search ............... 623/16.11, 18.11; 424/423, 422, 426; 523/115

(56) References Cited

U.S. PATENT DOCUMENTS

| 4,516,276 | A |  | 5/1985 | Mittelmeier et al. |
| 5,417,975 | A | * | 5/1995 | Lussi et al. ................ 424/423 |
| 5,573,771 | A | * | 11/1996 | Geistlich et al. ............ 424/422 |
| 5,899,939 | A | * | 5/1999 | Boyce et al. ............... 523/113 |
| 6,352,558 | B1 | * | 3/2002 | Spector .................. 623/18.11 |

FOREIGN PATENT DOCUMENTS

| EP | 0171176 | 2/1986 |
| WO | WO 8304177 | 12/1983 |
| WO | WO 9625961 A1 | 8/1996 |

* cited by examiner

Primary Examiner—David J. Isabella
Assistant Examiner—Kamrin R Landrem
(74) Attorney, Agent, or Firm—Rothwell, Figg, Ernst & Manbeck, p.c.

(57) ABSTRACT

A bone mineral product for use in repair of combined cartilage defects and bone defects in articulating bone joints includes porous bone mineral particles derived from natural bone having a crystal structure substantially that of natural bone and being substantially free from all endogenous organic material, the particles having at least at a surface thereof resorbable, physiologically compatible collagen II fibers wherein the weight ratio of the collagen II fibers to the porous bone mineral particles is at least about 1:40.

16 Claims, 1 Drawing Sheet

BONE MATERIAL AND COLLAGEN COMBINATION FOR REPAIR OF INJURED JOINTS

CROSS-REFERENCE TO RELATED APPLICATION

This application claims the benefit of provisional application Serial No. 60/219,009, filed Jul. 19, 2000.

BACKGROUND OF THE INVENTION

1. Field of the Invention

The present invention relates to the field of repair of injured or defective joints.

2. Description of the Background Art

Articulating joints in mammals are covered with articular cartilage which prevents direct contact of the opposing bone surfaces and permits smooth movement of the articulating bones relative to one another.

There have been several proposals for repair of injuries and defects in articular cartilage. These include implantation of cultured chondrocytes at the site of cartilage injury, and covering the injury with a collagen patch.

Sometimes the injury or defect in an articular joint extends deeper than the articular cartilage into the underlying bone. There remains a need in the art for materials and methods for repairing articulating joints in which an injury or defect extends through the cartilage into the bone.

SUMMARY OF THE INVENTION

In accordance with the present invention, a bone mineral product for use in treating combined cartilage and bone injuries or defects in articulating joints comprises porous bone mineral particles derived from natural bone having a crystal structure substantially that of natural bone and being substantially free from all endogenous organic material, the particles having at least at a surface thereof resorbable, physiologically compatible collagen II fibers wherein the weight ratio of said collagen II fibers to said porous bone mineral particles is at least about 1:40.

DETAILED DESCRIPTION OF THE INVENTION

Figure 1:
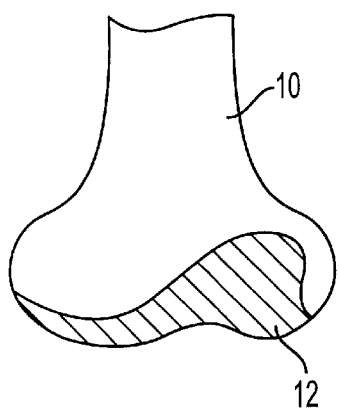
FIG. 1 is an elevational view, partly schematic, of an end of a healthy articulating joint bone.

The present invention is useful for reconstructing tissue defects involving both cartilage defects and bone defects, particularly in articulating joints such as the knee and spine.

The bone mineral product of the present invention, comprised of particles of porous bone mineral and collagen II fibers, provides a substrate for ingrowth of both native chondrocytes and native osteocytes into the matrix to affect cartilage and bone regeneration.

The collagen II matrix of the product of the present invention also imparts strength to the brittle bone mineral.

According to the present invention a purified particulate bone mineral product is provided for use in medicine, the particles of said mineral being substantially free from all endogenous organic material and having at least at the surface thereof resorbable, physiologically compatible, collagen II material.

Bones from slaughtered animals are an inexpensive raw material available in large quantities. They contain 50 to 60% of very finely crystallized hydroxylapatite bonded by collagenic tissue and containing significant qualities of proteinaceous and other matter as well as associated fat and muscle tissues. In view of its biologically formed crystal structure it can also be considered as a highly biocompatible prosthetic bone replacement. Owing to its large specific surface it can also be used, for example, as an adsorbent or as a support for slow release medication.

Natural bone mineral comprises hydroxyapatite like crystallites with a particular degree of crystallinity, habit and size (irregular plate-like morphology, 5–10 mm in thickness 10–50 mm in length) and surface chemistry resulting from the calcium to phosphate ratio (37.5–38.0% calcium and 15.5–19% phosphorus). Also present in the natural bone mineral are small amounts of noncrystalline entities and other calcium phosphate crystalline phase including the minerals Brushite and Nihitlockite, and octa-calcium phosphate. The inorganic phase of bone contains porosity including ultrastructural interstices (10–100 mm) between the crystallites occurring naturally and produced by removal of the organic phase, and microscopic spaces (1–20 microns, including osteocyte lacunae, canaliculi, vascular channels, Volkmann's canals, and the canals of Haversian systems (100–500 mm). The specific surface area, which is a measure of porosity is in the range 50 to 100 m2/gm as determined by mercury Porosimetrv. The crystallinity of bone mineral can he characterized by X-ray diffraction and the porosity and crystallite morphology and size by electron microscopy. Small amounts of nonapatitic crystallites can be detected by thermogravimetric analysis.

However, the composition and structure of natural bone mineral cannot be duplicated by products formed In vitro or by naturally occurring hydroxyapatites prepared previously. Two methods for the purification of natural bone mineral have been proposed, namely calcination and solvent extraction.

The temperature needed during calcination for the incineration of the organic constituents of the bones are rather high. This leads to extensive recrystallization of the mineral part with formation of much coarser crystals. The so formed material exhibits a relatively small specific surface. Thus, such material is not readily remodeled to form new bone on implantation and implants may remain unremodelled indefinitely although this may be acceptable for some purposes.

In the extraction processes the proteins are extracted from degreased bone with a suitable solvent. The resulting bone mineral is then washed to remove the solvent.

In both cases, when organic impurities are removed from the natural bone to leave only the bone mineral, the strength of the material is greatly reduced and the individual pieces of purified bone mineral are consequently extremely brittle.

This renders handling of the material difficult and may lead to undesirable effects on implantation.

Commonly owned U.S. Pat. No. 5,573,771 (incorporated herein by reference) discloses a medicinal bone mineral product in which the bone mineral is strengthened by a matrix made up of Type I collagen (collagen I), or a mixture of Type I collagen and Type III collagen (collagen I and collagen III).

Collagen occurs in a number of forms in the animal body, and different tissues contain different proportions of the respective types. Collagen sponge material used in medicine and in cosmetics is generally derived from skin and tendons, and is comprised predominantly of collagen I and/or collagen III. Bone collagen comprises predominantly collagen I and collagen II.

The collagen II material of the present may include, in addition to substantially pure collagen II, various proportions of collagen I, collagen III and mixtures thereof blended with the collagen II. For example, the collagen II material may have mixed therein about 0.1–10% by weight (preferably about 0.1–5% by weight) collagen III, and/or about 1–50% by weight collagen I.

The collagen II material of the present invention may impregnate each of the individual particles to improve the handling properties of the product in manufacture and use. In that case, the weight ratio of the collagen II material to the purified bone mineral is advantageously greater than 1:40, preferably greater than 1:8 and less than 4:1, preferably less than 1:2. Advantageously, the collagen II material comprises about 1–30% by weight of the bone mineral product of the present invention, preferably about 5–15% thereof. The collagen II material penetrates the porous structure of the bone mineral and effectively replaces some of the natural proteinaceous material previously present in natural bone which, although providing strength, also gives immunological tissue reactions on implantation of the bone mineral.

The collagen II material may be used to provide a matrix for the particulate bone mineral from which shaped articles may be formed. In this case, it is possible to use Collagen II together with a gel forming macromolecular substance such as gelatin. The weight ratio of the fibrous material to the bone mineral may, for example, be in the range 1:40 to 3:20 e.g. about 1:10. The gel phase advantageously amounts to 2 to 20% by weight of the bone mineral, e.g. about 5%. Where gelatin is used as the gel phase, it may be lightly cross-linked, e.g. with about 0.2% formaldehyde.

The bone mineral preferably is from spongiosa bone, and is linked with the collagen II fibers to add physical strength to the matrix. In preferred embodiments, the bone mineral/collagen product according to the present invention is used as a matrix to regenerate cartilage defects in articulating joints where additionally bone loss is present.

The bone mineral product according to the invention may be used for cartilage regeneration in knees, feet, spine, etc., and as a remodeling implant or prosthetic bone replacement, for example in orthopedic surgery including hip revisions, replacement of bone loss, e.g. in traumatology, remodeling in maxillo-facial surgery or filling periodontal defects and tooth extraction sockets, including ridge augmentation. The impregnated particulate material of the invention may thus be used for packing into a variety of bone cavities and its reduced brittleness is significant in aiding the handling and packing procedure.

In one method of the invention, the bone mineral product/collagen II material is inserted into a bone defect, and then the bone mineral/collagen II product and the bone defect are covered by a collagen membrane for tissue reconstruction. Suitable collagen membranes are known in the art, and can be a single layer collagen II membrane as taught in WO 96/25961 (U.S. patent application Ser. No. 08/894,517), a dual surface collagen I/III membrane as taught in U.S. Pat. No. 5,837,278, having a compact, smooth, non-porous outer barrier surface and an opposite soft fibrous surface, or a multi-layer membrane comprising an open, sponge-like collagen II matrix layer and at least one barrier layer of collagen I, collagen III or a mixture thereof as taught in U.S. patent application Ser. No. 09/545,465, filed Apr. 7, 2000, corresponding to PCT/GB98/02976, and the like. The above-referenced documents are incorporated herein by reference.

Figure 5:
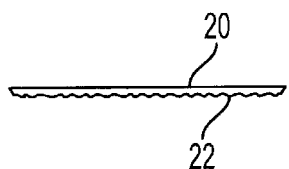
FIG. 5 is a schematic side view of a membrane for use in accordance with one embodiment of the invention.

In one preferred embodiment, the membrane has an outer smooth barrier surface which inhibits cell adhesion thereon and acts as a barrier to prevent passage of cells therethrough, and an opposite membrane face which is fibrous and soft so as to allow cell growth thereon. One such product is Bio-Gide® sold by Ed. Geistlich Söhne AG für Chemische Industrie of Switzerland. FIG. 5 shows the Bio-Gide® product, with the smooth outer barrier surface 20 and the soft fibrous surface 22. When utilized in accordance with the present invention, the soft, fibrous surface is applied toward the defect, with the smooth outer barrier surface directed outwardly. The Bio-Gide® product is described in U.S. Pat. No. 5,837,278 (supra), and is comprised of about 95–99% collagen I and about 1–5% collagen III.

Figure 6:
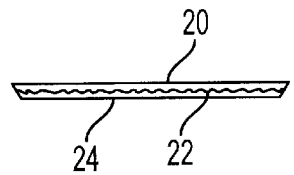
FIG. 6 is a schematic side view of another membrane for use in accordance with a second embodiment of the invention.

In another preferred embodiment, a multi-layer membrane is utilized in accordance with the present invention as described in the above-referenced U.S. patent application Ser. No. 09/545,465. Such a multi-layer membrane can be made by applying a collagen II slurry to the soft fibrous surface of the Bio-Gide® product described above. Such a product is shown in FIG. 6, and includes an outer barrier surface 20, and a matrix layer predominantly of collagen II having an open, sponge-like texture 24, which is applied as a slurry to the soft, fibrous surface 22 and then dried. When a product as shown in FIG. 6 is utilized in accordance with the present invention, the open, sponge-like collagen II layer 24 is applied to the defect, with the smooth outer barrier surface 20 being outwardly directed.

As noted above, the invention is particularly applicable to regeneration of articular joint defects in which both the cartilage and underlying bone is damaged. The bone mineral/collagen product of the invention can be utilized to fill in an area of bone damage, and the filled-in area of bone defect then can be covered with a collagen membrane.

To enhance regeneration, extracellular cultivated chondrocytes can be added to the bone mineral/collagen matrix of the invention before implantation, and the chondrocyte-charged matrix then can be implanted during open surgery or arthroscopic surgery. Alternatively, or in addition thereto, the implanted matrix can be covered with a collagen membrane comprised of collagen I, II and/or III, or covered by a synthetic membrane. Such collagen membrane or synthetic membrane can alternatively or additionally be charged with extracellular cultivated chondrocytes, with the membrane being applied over the filled-in bone implant by open surgery or arthroscopic surgery.

The purified bone mineral may, for example, be a product as described in International Patent Application WO 86/07265 (PCT/GB86/00310). Such products may be prepared by rigorously de-greasing particulate bone, e.g. bovine femurs, and treating with ammonia or an organic amine to degrade residual protein followed by extensive water washing. Such material remains resorbable on implementation, assisting the remodeling process.

It is also possible to prepare purified bone mineral by calcinating particulate cancellous or cortical bone e.g. at 900° C. for 24 hours. Such calcined bone mineral is of use where permanent, non-resorbable implants are required, for example in ridge augmentation. In either way after removal of organic material, the bone is excessively brittle and its strength is greatly improved by treatment according to the invention.

Where the bone is to be used as a drug carrier, as indicated in the above International Patent Application the bone mineral may usefully carry one or more absorbed drugs or other physiologically active substances. In accordance with one embodiment, the product of the invention comprises at least one absorbed pharmaceutically or biologically active substance or mesenchymal stem cells having an ability to differentiate into cells to regenerate cartilage or bone.

Physiologically active substances which may be adsorbed onto the bone mineral are preferably at least partially water-soluble and include antibacterial substances such as antibiotics e.g. penicillins, cephalosporin, aminoglycosides etc., sulphonamides and, in particular, condensation products of formaldehyde with taurinamide or N-substituted taurinamide. The latter compounds may be represented by the formula

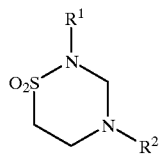

where $R^1$ is hydrogen or a $C_{1-4}$ alkyl group and $R^2$ is hydrogen or a group of the formula

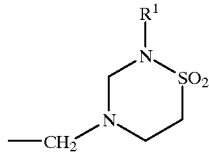

wherein $R^1$ has the above meaning.

The compound of formula (I) in which $R^1$ and $R^2$ are both hydrogen is taurultam while the compound in which $R^1$ is hydrogen and $R^2$ has the formula (II) is taurolidine. These compounds act as methylol transfer agents and are effective not only in destroying both gram negative and gram positive bacteria but also in inactivating both endotoxins and exotoxins produced by the bacteria.

Other useful physiologically active substances include proteins and polypeptides capable of assisting bone regeneration especially non-collagenous proteins derived from bone matrix and bone cells. These include mitogenic factors such as skeletal growth factor and morphogenic and angiogenic factors as well as transforming bone growth factor. Growth factors from the natural bone matrix such as ossein or more preferably osteopoietin are particularly beneficial.

According to one embodiment, a pharmaceutically active substance is selected from the group consisting of bone morphogenic proteins (BMPs) such as BMP-2–8, or other skeletal matrix molecules, as well as signaling peptides such as transforming growth factor-β TGF-β, TGF-β1, vascular endothelial growth factor (VEGF), insulin-like growth factor (IGF), parathyroid hormone related protein (PTHrP) and platelet derived growth factor (PDGF).

The product of the invention also may act as a carrier for stem cells committed to a particular line of differentiation such as articular cartilage or bone. Such stem cells may be grown in vitro to increase their numbers, and applied to the repair sites in the carrier matrices with or without growth factors.

It will be appreciated that physiologically active substances may alternatively or additionally be incorporated in the macromolecular substance e.g. impregnated gelatin. This is particularly suitable for proteins such as the bone growth factors set out above.

The bone mineral will normally be in the form of particles of average diameter in the range 0.1 to 10 mm. Particles for incorporation into collagen II fiber will preferably be of spongiosa bone and will generally be in the size range 0.1 to 5 mm, preferably 0.5 to 2 mm. It may be beneficial to the close packing of the bone mineral particles to use a mixture of two or more particle sizes, e.g. 0.25 to 1 mm and 1 to 2 mm or a broad range e.g. 0.25 to 2 mm.

The purified bone mineral may be obtained, for example, by the method described in the above International Patent Application. Thus, for example, fats may be removed using one or more conventional fat solvents such as ethers, e.g. dimethyl ether; ketones e.g. acetone; or hydrocarbons or halogenated hydrocarbons e.g. heptane or methylcylcohexane or toluene.

It may be advantageous to remove an extractant such as toluene by an intermediate extraction with a water miscible solvent such as ethanol before proceeding further. Collagen material may be dissolved using proteolytic agents such as bases e.g. Potassium hydroxide in glycerol, or organic bases such as amines, e.g. ethylene diamine, or amides such as formamide, preferably at elevated temperatures. Such agents are preferably water-miscible to facilitate removal by water washing. Especially good results have been obtained using bone extracted with refluxing ethylene diamine.

Extraction may advantageously be continued at each stage, if necessary with changes of solvent, until no further material is extracted, e.g. for periods up to one or two weeks. It may be advantageous to comminute further after initial protein removal since the bone is more readily fractured at that stage than before extraction. After treatment with base, excess solvents are rigorously removed e.g. by evaporation and/or, where suitable, water washing.

The material is normally subjected to a drying step. It may be convenient to sterilize the material at this stage, e.g. by heat treatment which may effect further purification. Absorption and/or adsorption of the physiologically active substance is preferably effected by immersing the treated bone mineral in an aqueous solution thereof preferable under sterile conditions. The concentration of the active substance is preferably relatively high to facilitate adsorption and/or absorption and will depend in part on the solubility of the active material.

The invention now will be further described with reference to the drawings.

FIG. 1 shows an end of an articulating bone 10 with cartilage 12, which is healthy and without defect.

Figure 2:
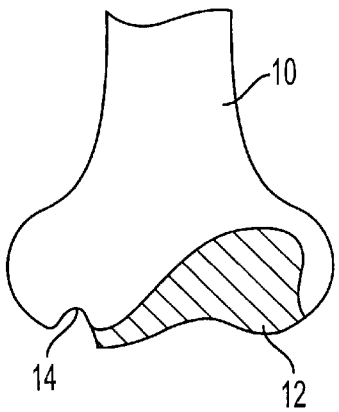
FIG. 2 is an elevational view, partly schematic, of an end of a articulating joint bone in which a defect is present extending through the cartilage into the bone.

FIG. 2 shows an articulating bone 10 with cartilage 12 in which a defect 14 extends through cartilage 12 into bone 10.

Figure 3:
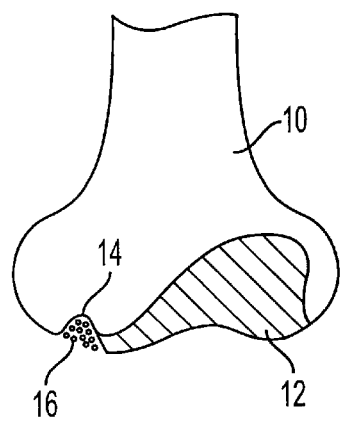
FIG. 3 is an elevational view, partly schematic, in which a bone mineral/collagen matrix in accordance with the present invention has been inserted into a defect in an end of an articulating joint bone.

FIG. 3 shows the bone mineral/collagen matrix 16 of the invention, which may be charged or uncharged with chondrocytes, and filled-in to the defect 14 in cartilage 12 and bone 10.

Figure 4:
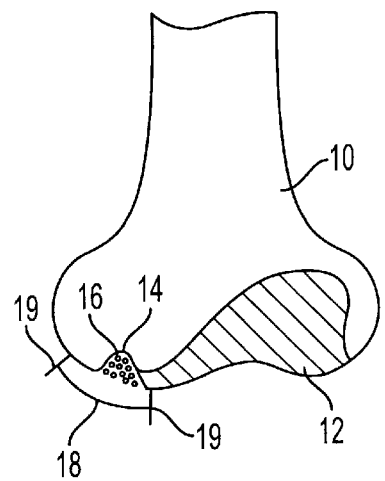
FIG. 4 is an elevational view, partly schematic, in which a collagen or synthetic membrane is covering a joint defect which has been filled-in with a bone mineral/collagen matrix according to the present invention.

FIG. 4 shows a collagen or synthetic patch 18 which may or may not be charged with chondrocytes, covering defect 14 filled-in with new bone mineral/collagen matrix 16 of the invention, for regeneration of the injury to both the cartilage 12 and bone 10. Patch 18 can be attached by any suitable means 19, such as sutures, surgical nails or adhesive.

FIG. 5 is a schematic side elevation view of a membrane according to one embodiment for use in accordance with a method of the present invention.

FIG. 6 is a schematic side elevation view of another membrane according to a second embodiment for use in a method according to the invention.

The following Examples are given by way of illustration only:

EXAMPLE 1

Bovine femur bones were boiled in hot water until clean, comminuted to a particle size of 5 to 10 mm. and extracted under reflux with toluene for 24 hours in a Sohxlet apparatus. The material was further extracted with ethanol to remove toluene and then extracted at elevated temperature with an azeotropic mixture of ethylene diamine and water (85:15) for 8 days, with several changes of solvent until substantially no further organic material was extracted. The product was then air dried at 100° C.

The dried product was further comminuted to an average particle size of 0.2 to 2 mm and sterilized in the autoclave. Pieces of bovine femur spongiosa bone, typical diameter 10 mm, were purified by the same technique, omitting the final granulation.

EXAMPLE 2

Frozen cartilage from freshly slaughtered pigs was steeped in cold water, thoroughly washed through and mechanically purified from flesh residues, bones and hard pieces. Subsequently, the material was washed for 30 minutes under flowing water.

Subsequently, the material was ground three times in a homogenizer. The optimal particle size at the end of size reduction was about 8 mm.

The cartilage pieces were dewatered by washing 4 times with acetone, each time for 8 hours. The cartilage was then defatted by extraction 4 times with n-hexane. Each treatment lasted at least 8 hours. The ratio of hexane to cartilage was 1:10.

After defatting, the cartilage was swelled in drinking water. The ratio of water:material was 10:1. The treatment time was 24 hours.

The material was then treated with NaOH (5% by weight) whereby the ratio of cartilage to liquid was 1:4 and the treatment time was 32 hours. During the treatment, the pieces of cartilage were well stirred. Subsequently, the alkali was washed from the cartilage. The original pH of 14 was thereby reduced to 9–11. The dissolved impurities were washed out and separated from the cartilage. The liquid resulting from the alkaline treatment was collected for the recover of glycosaminoglycan.

The collagen material was then treated with strong HCl (about 3% by weight) initially at a pH value under 1.0. The treatment time was 4–6 hours.

Subsequently, the material was washed with cold water long enough for the pH value to rise to 3–3.5. All impurities were removed and the product was a salt-free collagen mass, suitable for production of a sponge or other collagen material. For that purpose, the collagen mass may be, according to the intended result degassed, frozen and freeze-dried.

EXAMPLE 3

The extract resulting from alkaline treatment in Example 2 contained glycosaminoglycan, alkali, denatured proteins and salts. The extract was firstly neutralized with HCl, the pH value after neutralization being 6. The extract was then treated with a filter aid, namely kieselguhr, which had the effect of removing the denatured proteins. 0.5 weight percent of kieselguhr was introduced into the extract and removed by filtration together with the denatured protein.

The supernatant was then submitted to ultrafiltration using a membrane having a molecular weight cut off at about 10000 Daltons. In this way, salts were removed to leave purified glycosaminoglycan.

The glycosaminoglycan solution so obtained was admixed with collagen material from above to provide a collagen II matrix containing glycosaminoglycan.

EXAMPLE 4

2.0 g of collagen II material from Example 3 is comminuted with 500 g distilled water in a blender. This dispersion is centrifuged and the supernatant water removed. To the resulting collagen fiber slurry is added 17.5 g of granulated cortical bovine bone purified by the above procedure of Example 1, followed by thorough mixing and removal of water by suction (70 mm). The granulated bone has a particle size 0.5 to 1.0 mm. After removal of water, 5 mls of a 9% w/w aqueous gelatin solution are added (cross-linked with 0.6% of 35% aqueous formaldehyde) and the mixture again suction dried.

The sponge mass is cut into pieces and dried in vacuo at 60° C. The pieces of sponge are packed into polyethylene containers and sterilized by gamma irradiation.

What is claimed is:

1. A particulate bone mineral product for repair of combined cartilage defects and bone defects, the product comprising porous bone mineral particles derived from natural bone having a crystal structure substantially that of natural bone and being substantially free from all endogenous organic material, the particles having at least at a surface thereof resorbable, physiologically compatible, collagen II fibers, wherein the weight ratio of said collagen II fibers to said porous bone mineral particles is at least about 1:20.

2. The product of claim 1 wherein said particles have an average diameter in the range of about 0.1 to about 5 mm.

3. The product of claim 1 which further comprises at least one absorbed substance selected from the group of pharmaceutically active substance and isolated biologically active substance or mesenchymal stem cells having ability to differentiate into cells to regenerate cartilage or bone.

4. The product of claim 3 in which said pharmaceutically active substance is selected from the group consisting taurolidine, taurultam and a mixture thereof.

5. The product of claim 1, further comprising gelatin in a gel phase, wherein said collagen II fibers are present in said gel phase, and wherein said gel phase comprises about 2–20% by weight of the bone material.

6. A method of treatment of a human or animal subject wherein a bone mineral product as claimed in claim 1 is implanted into a combined cartilage defect and bone defect in a patient.

7. The method of claim 6, wherein the combined cartilage defect and bone defect is located in a joint end of an articulating bone.

8. The method of claim 6, further comprising inserting said bone mineral product into a bone defect and then covering said bone mineral product and said bone defect with a collagen membrane.

9. The method of claim 8 wherein said collagen membrane is comprised of a layer of collagen II.

10. The method of claim 8 wherein said membrane comprises a matrix layer predominantly of collagen II and having an open sponge-like texture, and at least one collagen barrier layer having a compact smooth barrier surface.

11. The method of claim 8 wherein said barrier layer is predominantly selected from the group of collagen I, collagen III or a mixture thereof.

12. The method of claim 8 wherein said membrane comprises a matrix layer predominantly of Collagen II and having an open sponge-like texture applied to a soft fibrous layer of a collagen I/III membrane having a compact smooth barrier surface opposite said matrix layer.

13. The product claim 3 in which said pharmaceutically active substance is selected from the group consisting of bone morphogenetic proteins (BMPs), other skeletal matrix molecules, and signaling peptides.

14. The product of claim 13 wherein said pharmaceutically active is selected from the group consisting of BMP-2-8, TGF-β, TGF-β1, VEGF, IGF, PTHrP and PDGF.

15. The product of claim 3 further comprises isolated articular cartilage stem cells or bone stem cells.

16. The product of claim 1 wherein said collagen II fibers are derived from cartilage.

\* \* \* \* \*

UNITED STATES PATENT AND TRADEMARK OFFICE
CERTIFICATE OF CORRECTION

PATENT NO. : 6,576,015 B2
DATED : June 10, 2003
INVENTOR(S) : Geistlich et al.

It is certified that error appears in the above-identified patent and that said Letters Patent is hereby corrected as shown below:

<u>Column 8,</u>
Line 9, "1:20" should be -- 1:40 --; and
Line 2, after "active" insert -- substance --.

Signed and Sealed this

Eleventh Day of May, 2004

JON W. DUDAS
*Acting Director of the United States Patent and Trademark Office*